United States Patent [19]

Hicks

[11] Patent Number: 5,133,035

[45] Date of Patent: Jul. 21, 1992

[54] MULTIFIBER ENDOSCOPE WITH MULTIPLE SCANNING MODES TO PRODUCE AN IMAGE FREE OF FIXED PATTERN NOISE

[76] Inventor: John W. Hicks, 312 Howard St., Northboro, Mass. 01532

[21] Appl. No.: 673,650

[22] Filed: Mar. 22, 1991

Related U.S. Application Data

[63] Continuation-in-part of Ser. No. 436,446, Nov. 14, 1989, Pat. No. 5,074,642.

[51] Int. Cl.⁵ .............................................. G02B 23/26
[52] U.S. Cl. .................................... 385/117; 385/119
[58] Field of Search ............... 350/96.24, 96.25, 96.26; 355/1; 385/115, 116, 117, 118, 119

[56] References Cited

U.S. PATENT DOCUMENTS 5,015,064   5/1991   Detig et al. ...................... 350/96.25

FOREIGN PATENT DOCUMENTS 1171552   11/1969   United Kingdom ............. 350/96.25

Primary Examiner—John D. Lee
Assistant Examiner—John Ngo
Attorney, Agent, or Firm—Samuels, Gauthier & Stevens

[57] ABSTRACT

A fiberoptic endoscope scanning system with multiple scanning modes. A first mode is a multifiber scanning about its longitudinal axis and a second scanning mode is a chromatic scan, comprising a prism and/or grating at the distal end.

23 Claims, 3 Drawing Sheets

MULTIFIBER ENDOSCOPE WITH MULTIPLE SCANNING MODES TO PRODUCE AN IMAGE FREE OF FIXED PATTERN NOISE

CROSS REFERENCE TO RELATED APPLICATION

This application is a continuation-in-part application of Ser. No. 436,446 filed Nov. 14, 1989, now U.S. Pat. No. 5,074,642.

FIELD OF THE INVENTION

The present invention relates to endoscopic devices and in particular to a scanning multifiber endoscope which eliminates the noise pattern inherent in prior art fiber optic or multifiber endoscopes.

BACKGROUND AND BRIEF SUMMARY OF THE INVENTION

The transmission of light through thin fibers of glass or plastics has resulted in a variety of instruments for the visualization of otherwise inaccessible organs and tissues inside the human body. Such instruments are broadly referred to as endoscopes and have been useful in the diagnosis and treatment of, for example, gastro intestinal and respiratory diseases.

Fiberoptic endoscopes were first introduced about thirty years ago. Although they have gained wide acceptance where flexibility is required, medical personnel still prefer to use rod lenses or other alternatives. The reason being that they are annoyed by the fixed mosaic structure of a fiberoptic image. Also in most applications, the resolution of present fiberoptic endoscopes is generally inferior to other alternatives.

It is known in the art to scan with fiberoptics. If a multifiber is rotated, a concentric noise pattern is superimposed on the image. If the multifiber is not moved, a mosaic-like noise pattern is superimposed on the image.

In my parent application, a multifiber endoscope was disclosed with much improved resolution for a given diameter and which partially eliminated the fixed pattern noise typical of fiber endoscopes. However, I have found that even with rotational scanning there is still a residual fixed pattern streakiness comprising concentric circles even though the individual fibers themselves are no longer visible. Also, a small area near the axis of rotation has a very pronounced fixed pattern noise.

My present invention embodies a multiple-scanning technique for a multifiber which substantially reduces or eliminates the noise inherent in prior art multifiber endoscopes. The multiple scanning may comprise either a rotary and a chromatic scan or two rotary scans. In principle, many scanning combinations are possible but some scanning motions are difficult to achieve in a thin needle inserted into the body.

Rotary scan is particularly easy to achieve because the scanning motion at the distal end of the multifiber is driven by the torsion of the thin member itself and synchronism between the scan at the proximal and distal ends is almost guaranteed. Even a double rotary scan can be achieved. One example is a small eccentric rotation at one speed around a first axis superimposed over rotation at another speed around a second axis. That is, there is one rotation about a first axis and then rotation about another axis slightly displaced from the first axis and at, for example, one-tenth or ten times the angular velocity. To accomplish this, the fiber structure may rotate in a sleeve which has an eccentric bore which rotates in another sleeve.

In a preferred embodiment, the multiple scanning is achieved by using a rotary scan in combination with a prism and/or grating to provide a chromatic scan. The field of view is tipped and rotated. This chromatic scan can be accomplished by attaching a prism or blazed grating to the sleeve in which the fiber rotates and then rotating the sleeve so the image is scanned in a rotational pattern on the face of the fiber while the fiber rotates. The prism, at the distal end, spreads an image point into a linear rainbow and creates the equivalent of a linear scan. A prism at the proximal end rectifies the image back from a rainbow to a point. In transit, each original point travels through many fibers along the length of the rainbow. The final result is much the same as if there were a linear scan in the plane of the tipped axis. Even if the prism is not rotated, only the fiber itself being rotated, two scans have been accomplished—a rotary scan and the linear chromatic scan. This chromatic scan per se has been known to the art for several years and it leaves linear streakiness. The combination of the two scans gives a much improved appearance.

If the prism rotates with the fiber, there is still a rotational and chromatic scan. If the prism rotates at a different angular velocity (from the fiber), there is actually a triple scan—one linear chromatic scan and two rotational scans.

The tip angle provides for flexibility in the field angle if that is desired. Gratings also tip the field angle and give much greater dispersion than the prism and can also be used for chromatic scanning. Because the grating dispersion and prism dispersion are of opposite effects, it is possible to combine a prism and a grating to get no tip and a lot of dispersion or a lot of tip and a little dispersion or any combination therebetween.

In one aspect of the invention, the optics can look straight ahead with no increase in the field of view and not rotate the prism/grating but rotate the fiber and get a combination of chromatic and rotational scan.

In another aspect of the invention, the field angle can be tipped and the prism/grating not rotated (not expand the field of view but only tip it) to get a combination of rotary scan and chromatic scan.

In another aspect of the invention, in addition to the rotary scan of the multifiber, a prism/grating can be rotated to expand the field angle and have a double scan, if the prism and fiber are synchronized, or a triple scan, if they are not synchronized. In all embodiments, there is a proximal set of lenses, prism/grating conjugate to the distal optics to produce a still image.

DESCRIPTION OF THE PREFERRED EMBODIMENT(S)

In the following disclosure, various combinations of multifibers, lenses and/or prisms and/or gratings will be described with reference to multiple scans. Structures to effect simple rotary scans of multifibers with lenses either adapted for rotation with the multifiber or fixed with reference to the multifiber are well known and need not be described in detail. Further, the techniques for the illumination of the object to be viewed and the various schemes for processing the signals received from the viewed object and to display the object are well within the skill of the art.

The multifiber described herein for the preferred embodiment has the optical characteristics of the multifiber in my parent application, namely the fibers having distinct indices of refraction. Although this form of multifiber is preferred, multifibers wherein each of the fibers have the same indices of refraction can be used or combinations of fibers having different refractive indices can be used in different arrays. Where necessary, for a full understanding of the invention, the specific optical properties of lenses, gratings and/or prisms are described.

It is known that the field of view can be increased by tipping, such as with a mirror. However to tip 45° and still be able to view in the forward direction is not easy to do with any simple array of mirrors that do not take up a lot of space.

An ordinary diffraction grating, generally will look both ways unless it is blazed to look preferentially in one or the other direction. If the diffraction grating is made holographically, then blazing is easily accomplished. In any case, unwanted negative orders can be further suppressed by illuminating only in the desired direction. Both the prism and the grating have strong chromatic effects. In the case of the prism, the blue light is tipped more than the red light and in the case of the grating, the red light is tipped more than the blue light. These chromatic effects are corrected for at the proximal end.

With the structure to effect the tipping action, a chromatic scan is also accomplished. Chromatic scan, as used in the disclosure, defines the optical spread of the wavelengths. Because the image of one point is spread out in a rainbow and then travels through many fiber cores, the effect is much the same as if the fiber had been scanned in the tipped direction. When the final image is viewed, the fiber core structure almost disappears and the resolution is increased almost as if the bundle had been rapidly scanned. There is still linear streaking parallel to the scanned dimension just as there is with a one dimensional scan. However, if the fiber is scanned about its axis this linear streakiness also disappears.

Figure 1:
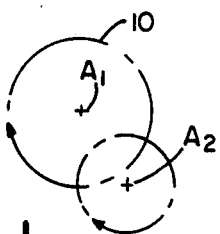
FIG. 1 is an illustration of a multifiber with two rotary scans.

Referring to FIG. 1, an example of multiple rotary scanning is shown. A multifiber 10 rotates about a first axis identified as $A_1$. This axis $A_1$ then rotates about a second axis $A_2$.

Figure 2:
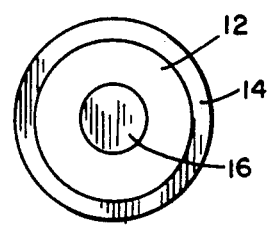
FIG. 2 is an illustration of a device used to effect the scans of FIG. 1.

Referring to FIG. 2, a device for accomplishing this multiple rotary scan is shown. The multifiber 10 is received in a sleeve 12 which, as shown, has an eccentric bore which rotates in an outer sleeve 14.

Figure 3:
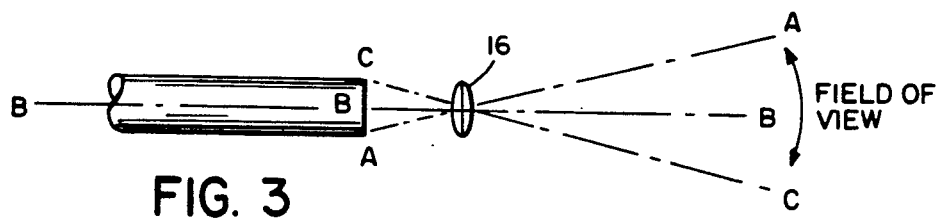
FIG. 3 is an illustration of a multifiber and lens.

Referring to FIG. 3, the multifiber 10 is shown in combination with a lens 16. The central ray is shown as B and the field of view is defined by A–C.

In the preferred embodiment, either a prism and/or diffraction grating (prism/grating) is used in combination with the multifiber to tip the central ray(s) and thereby expand the field of view. Normally, the central ray in a multifiber endoscope is coincident with the fiber axis. In the present invention, the central ray tipped away from the fiber axis and the ray is also dispersed.

Figure 4:
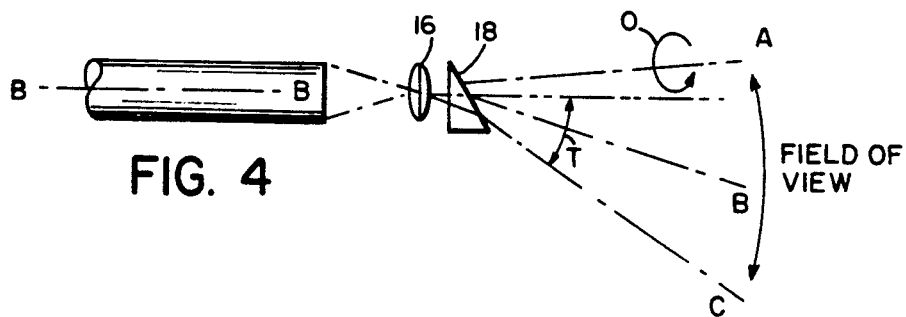
FIG. 4 is an illustration of a multifiber and lens and prism with a tipped field of view.

Referring to FIG. 4, a prism 18 tips the field of view. The tip angle is shown as T and the field of view is defined, as in FIG. 3, A–C. As the device of FIG. 4 is rotated about the longitudinal axis of the multifiber, as can be seen with reference to FIG. 4, a much larger field of view is swept.

Where A is tipped to be coincident with the axis of rotation B—B of the multifiber, the field of view is doubled.

If A is tipped more than this, below B—B with reference to FIG. 4, there will be a black hole in the image.

If A is tipped less than this, the image will be brighter in the area that is overlapped. This overlapped area is shown by the arrow O in FIG. 4. This can be partially compensated for by providing less illumination in the overlapped area of the object or by image processing (when the display is video, not directly viewed).

Figure 5:
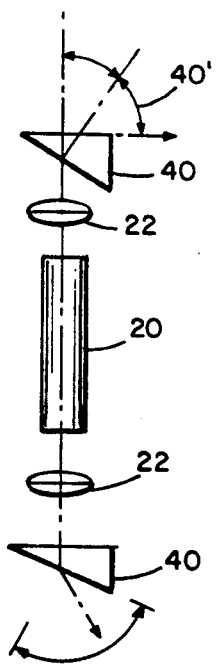
FIG. 5 is a schematic illustrating an image produced on the tip of the fiberscope.

Referring to FIG. 5, in one embodiment of the invention, a multifiber 20 has at the proximal and distal ends, lenses 22, 0.5 mm diameter and a refractive index of 2.0. For rotation with the multifiber 20 and the lenses 22 are 35° high dispersion prisms 40 having a refractive index of 1.8 which tips the field of view 30.5°. The multifiber is as described in my parent application. However, it is to be understood that any multifiber where the fiber cores have the same or different refractive indices may be used. A suitable multifiber having fiber cores of the same refractive index would be a commercially available multifiber, such as a Sumitomo multifiber.

Figure 6:
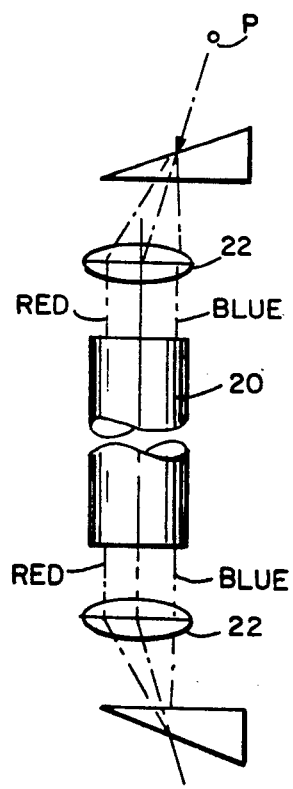
FIG. 6 is a schematic of an optical arrangement where the fiberscope is focused at a finite object.

Referring to FIG. 6, the image produced on the face of the multifiber 20 by a point object, P, at infinity is shown. The point, $P_1$, is spread into a linear rainbow. At the proximal end, the rainbow is recombined to form the point, P. The same spreading and recombining is true of a grating. Obviously the optics at the proximal and distal ends need to be identical or at least conjugal.

Figure 7:
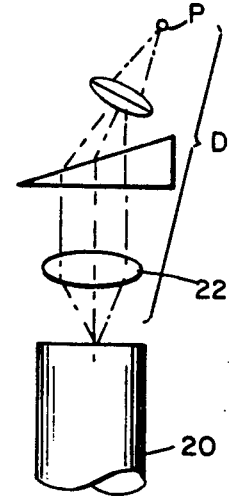
FIG. 7 is a schematic of a diffraction grating prism combination.

The prisms or gratings produce aberrations if the lens does not focus the face of the bundle to infinity. These aberrations are severe astigmatisms and something comparable to spherical aberrations. If the instrument must be focused to a finite object at a distance, D, of say 1 cm, referring to FIG. 7, another lens 42 is added. The lens 42 has a focal length of 1 cm to accommodate the object. Again the same optics is provided at the proximal end in that the optics must be identical up through the prism or grating but not necessarily beyond that.

When the multifiber looks straight forward or is only slightly tilted and a chromatic scan is used, a combination of a prism and a grating can be used. The prism has much less dispersion (much less spread in angle between red and blue) for the same tip angle than has the grating.

Little or no tipping with increased dispersion, for chromatic scanning, is achieved. The prism is preferably a high index glass. Such glasses are characteristically absorbing in the visible spectrum but the prism thickness is exceedingly small because of the small diameter of the fiberscope. So, absorption isn't a problem. Indices of refraction of 1.8 are commercially available.

Endoscopes of the invention are preferably designed so that they can be easily inserted into and removed from a sleeve such as a hypodermic needle. In this way a needle is inserted into a cavity in a body. A first endoscope is inserted with a nearly hemispheric field of view. When something of particular interest is sighted, the first endoscope can be removed and replaced by another endoscope with a narrower field of view, desired degree of tip and more pixels per unit object area (orientated or tilted in the direction desired). The fiberoptics is relatively inexpensive so these endoscopes can be made as disposable endoscopes.

When using combinations of prisms and gratings, there are certain design considerations. To a first approximation, a holographic grating which tips the principle ray of green light by 45° at the distal end of the endoscope and a holographic grating which tips the principle green ray 22½° at the proximal end together with a distal lens and a proximal lens with a focal length ratio of ½ will be a conjugate pair and accomplish the desired result. But to a closer approximation since $\theta$, sin $\theta$ and tan $\theta$ are not linear functions of each other, this is not exactly true. There are several options. The simplest is to select a second grating which collapses the rainbow fairly accurately and to forget the criteria of keeping any axes of rotation aligned. This will smear and distort the straight ahead part of the image. However, this may be acceptable in some cases. In the body, the dominant color is red. So a good compromise is to collapse the red end of the spectrum accurately at the expense of the blue end. The compromise can be tuned to the actual use.

A particularly preferred embodiment is to use a prism and holographic grating in combination at the proximal end, the grating used mainly to collapse the chromatic scan and the prism used to correct any residual tilt error.

Figure 8:
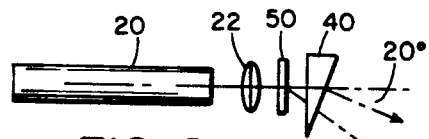
FIG. 8 is an illustration of the angular tilt of a prism.

The index of refraction of common glasses changes by 0.01 to 0.04 from the red end to the blue end of the visible spectrum. The higher dispersion glasses (0.03 for example) are called 'flints' and the lower dispersion glasses are called 'crowns'. The angular tilt produced by a prism is approximately $d=(n-1)\theta$ where $\theta$ is the prism angle and n is the index of refraction, see FIG. 8.

The spread in this angle from red to blue is the change in the index times $\theta$ $$\Delta d = \Delta n \theta$$

The ratio of $$\frac{\Delta d}{d} = \frac{\Delta n}{n-1}$$

Figure 9:
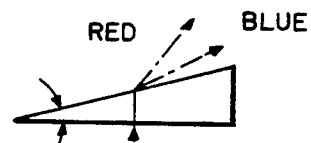
FIG. 9 is an illustration of the angular tilt of a grating.
Figure 10:
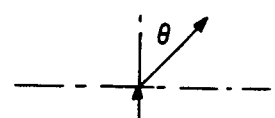
FIG. 10 is a schematic of alternative optics at a proximal end.

This range is from about 1/50 to 4/50
The tilt angle for a grating is shown in FIG. 9 where $$d \sin \theta = \lambda$$

so that for small $\theta$
The change in $\theta$ from red to blue is $$\Delta \theta = \frac{\Delta \lambda}{d}$$

and $$\frac{\Delta \theta}{\theta} = \frac{\Delta \lambda}{\lambda} =$$

which is about 0.5.

With these factors in mind, the tipping and chromatic scan can be tailored for specific viewing situations. The prism can be treated as almost non-dispersive in the first iteration of a design process. For a more precise approximation, the dispersion of the prism can be factored back in. Although it is of the opposite sign to that of the grating and is not the exact shape, it is possible to get an exact combination of tipping and dispersion at two points of the spectrum and have only a small uncorrected deviation in the spectral region between the two points.

At the proximal end, because $\theta$ is demagnified (by a factor of two for example) relative to the distal end, a combination of prism and grating (and lens focal length) can be found which gives the right tilt and collapses the chromatic scan at two spectral points but with some residual chromatic spread between these spectral points. Those skilled in chromatic aberration and lens design will understand how to make further corrections, for example by using a prism made of two glasses.

Figure 11:
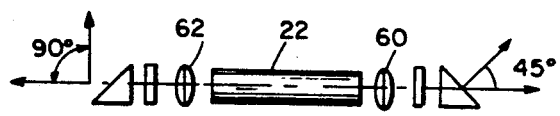
FIG. 11 is a schematic of alternative optics at the proximal end.

In another embodiment, FIG. 11, the problem of scanning out nearly a hemisphere and presenting an image which can be viewed at the proximal end is handled by using a lens 60 at the proximal end with twice the focal length of the lens 62 at the distal end. The longer focal length reduces the field angle and therefore reduces the tilt necessary to keep an axis of rotation at the far end and the axis of rotation at the near end aligned. The 90° total spread at the proximal end is fairly easy to catch with a field lens by conventional lens designs. As disclosed herein, this design collapses the rainbow generated by a ray at angle $\theta$ at the far end into a ray at the near end so an object point becomes a final image point not a rainbow. The problem of field angle correction is less severe if the final image goes to a video camera.

Figure 12:
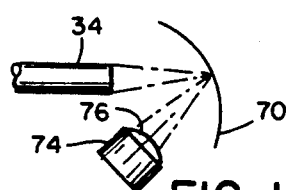
FIG. 12 is a schematic of a distortion pattern.

Referring to FIG. 12, a distortion pattern is shown. The axis of rotation is identified as $A_3$. Distortions in the X dimension are benign but the distortions in the Y dimension create blurring as the scan proceeds. Where the proximal optics are exactly conjugate to the distal optics, the distortion is rectified and there is no problem. In an embodiment where the proximal optics has a first lens with twice or more the focal length of the corresponding distal end, as described above, then the distortion will not be conjugate and this will result in blurring in the Y dimension as the scan proceeds.

Figure 13:
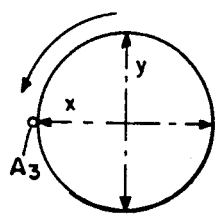
FIG. 13 is a schematic of a corrected distortion pattern.
Figure 14:
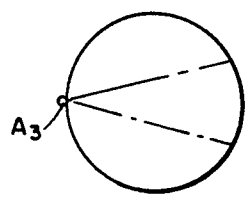
FIGS. 14, 15, 16, 17 and 18 are schematics of illumination and viewing schemes.

To overcome the distortion in this latter situation, referring to FIG. 13, the area to be used on the multifiber face is masked down. As shown in FIG. 14, the shaded area is masked. The distortion is reduced as the extent of the Y dimension is decreased. Such masking is also useful in achieving more uniform illumination. With this objective in mind, the unmasked area preferably is pie-shaped. This results in less total image brightness but again, if the illumination is made brighter (per unit area) but is reduced in total area and scanned in synchronism with the image scan, then the net use of illumination light is not reduced.

In use, the distal and proximal ends of the multifiber rotate in synchronism. The distal ends of the cores scan the image plane and the scanned image is returned via the fiber cores to the proximal end where the image information is read by a CCD array (or other video camera).

When illumination is carried down the same path by which the image returns there are problems with unwanted reflections and scattering—as in any other endoscope. In addition to the usual solutions to the illumination problem, there is one embodiment of this invention which is particularly useful when the scanning multifiber is masked to reduce distortion smear, as shown in FIG. 14.

Figure 15:
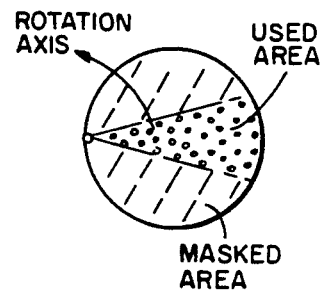

In this preferred illumination scheme a nearly identical rotating fiber distal lens, and prism is used rotating in synch with the viewing fiber, as shown in FIG. 15.

In this way, the area illuminated nearly coincides with the area viewed at any moment. This reduces the amount of light pumped into the body. Since the amount of illumination required may be near the damage threshold of some tissue this scheme gives a nontrivial advantage.

Figure 16:
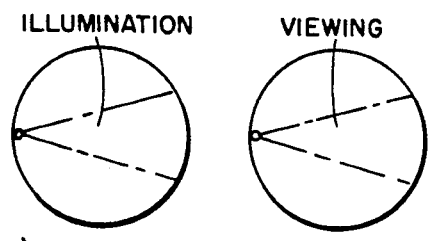
Figure 17:
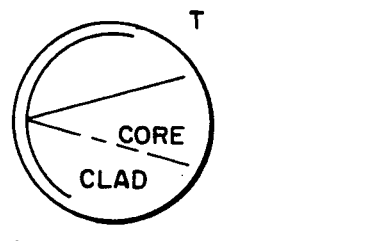

The illumination fiber need not have multiple cores, but is preferably as shown in FIG. 16. The whole pie shaped region is a core surrounded by a lower index glass (or plastic).

Figure 18:
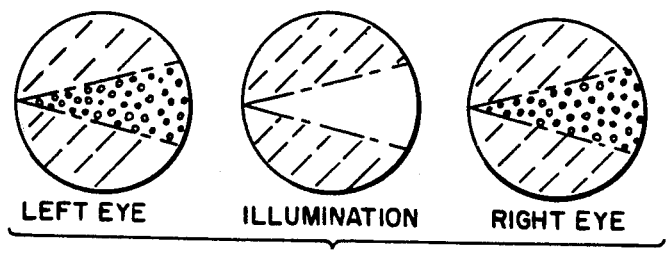

When the endoscope is to provide a stereoscopic image, a central illumination services both viewing channels, as shown in FIG. 18.

The prior art relating to illumination of fiber bundles, particularly in endoscopes, and the viewing and display of viewed objects is well known in the art and need not be described in detail.

Figure 19:
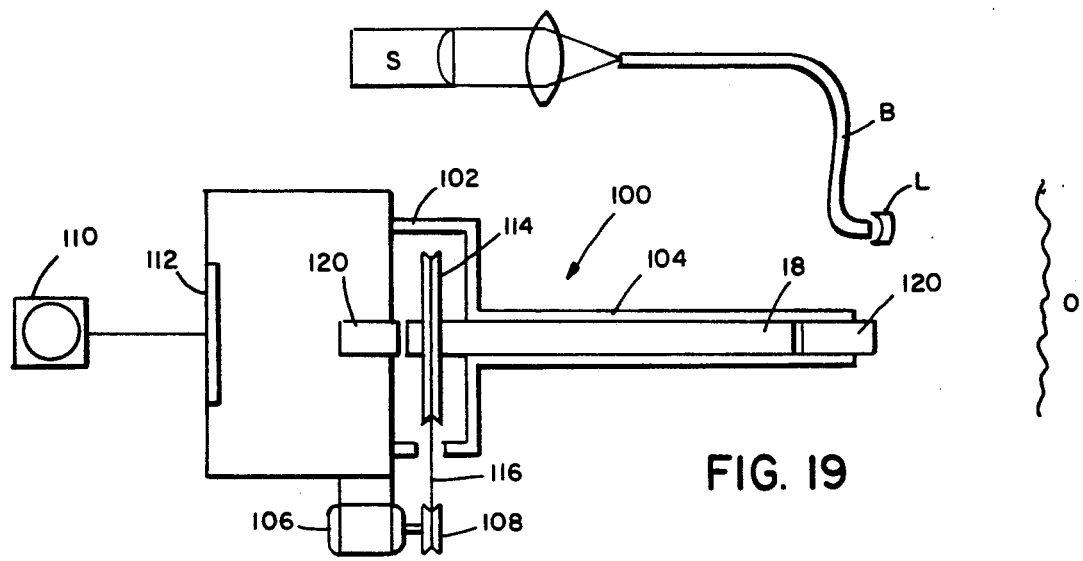
FIGS. 19, 20 and 21 are illustrative of endoscope systems embodying the invention.

FIG. 19 shows a system where only the fiber rotates together with the proximal and distal optics and comprises a housing 102 including an extending sleeve 104, a motor 106 with an associated pulley 108. The housing 102 also supports a video camera 110 with a CCD array 112. The multifiber 20 is rotatably received in the sleeve 104. Bearings or the like (not shown) may be used to facilitate rotation of the multifiber 20. Also, collars and the like may be used in the housing to prevent longitudinal movement of the bundle. Secured to the bundle for rotation therewith is a pulley 114 which is rotated by a drive belt 116 secured to the pulley 108. A Selfoc lens 22 is secured to the housing at the proximal end and a Selfoc lens 120 is secured to the sleeve at the other end.

Fiber optic illuminations using incandescent or arc-light sources are well known and commercially available. An alternate but expensive source is a white dye laser or a combination argon and krypton laser balanced to provide quasi white light. The illumination can be delivered by an entirely separate probe inserted percutaneously into the body cavity or by an illumination channel lying beside or surrounding the viewing fiber optic bundle. The various possibilities are well known to the art. The present invention has the advantage of having a very small cross section (for its high resolution) and it is desireable not to enlarge the cross section unnecessarily with an illumination channel. It is therefore very advantageous to use a very bright light source, such as a laser, in order to be able to minimize the area of the illumination channel. Shown in FIG. 19 is an illumination scheme. A fiber optic bundle B and lens L illuminates the object O to be viewed. A solid state pick-up device, such as the CCD 112, communicates with the TV monitor. Alternatively, a laser beam, such as from a dye laser, may be used for illumination. These illumination sources can be used in the embodiments of FIGS. 20 and 21.

Figure 20:
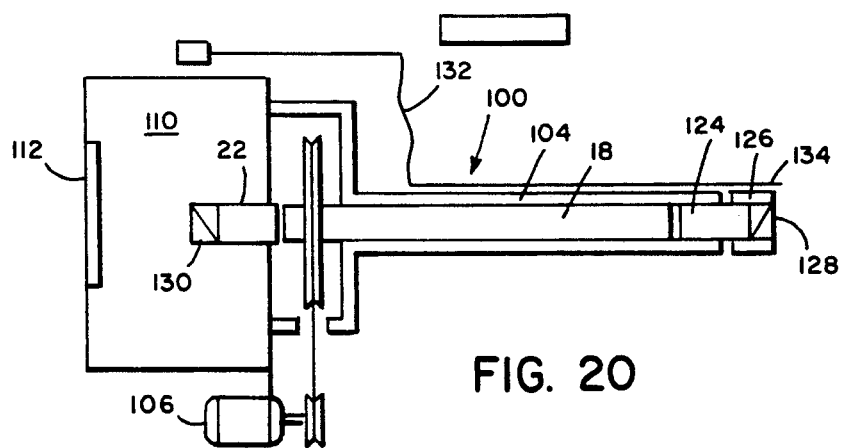

Referring to FIG. 20, a similar structure is shown as for FIG. 19. However, in this embodiment, the multifiber 20 rotates together with the proximal and distal optics at a speed of about 5 to 30 rps. In this embodiment, the selfoc lens 22, 0.5 mm diameter, refractive index 2.0, at the proximal end is adhered to the fiber bundle 20 for rotation therewith. This lens has about twice the focal length of a distal selfoc lens 124. This distal lens 124 is adhered to the fiber bundle 20 for rotation therewith. Secured to the extending portion of the lens 124 for rotation therewith is a sleeve 126 in which is secured the prism 40, which tips the field of view 30.5°. At the proximal end of the fiber bundle 20 and secured to the lens 22 for rotation therewith is a prism 130, which tips the field of view about half the angle of the prism 128. Therefore, in this embodiment, the prism 130, lens 22, fiber bundle 20, lens 124 and prism 128 all rotate. A single fiber laser 132 is secured to the outer surface of the sleeve 104. Its end 134 is shaped to illuminate the entire area to be viewed.

Figure 21:
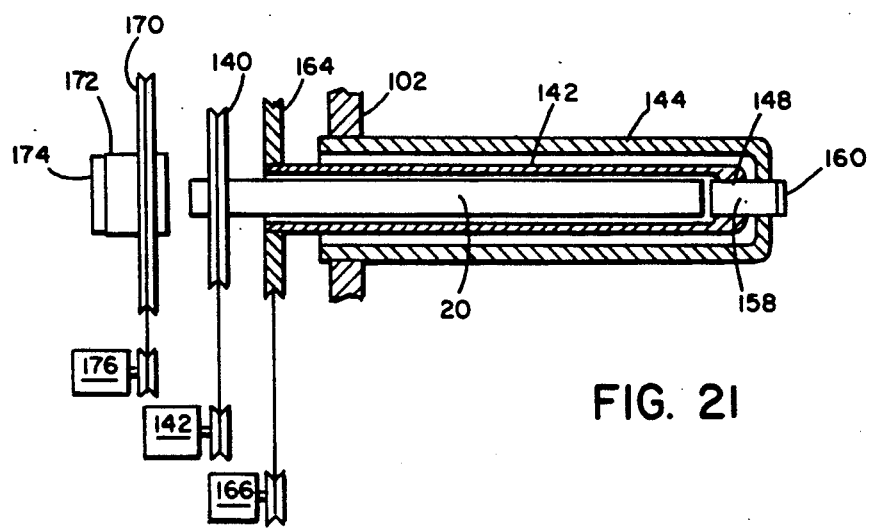

Referring to FIG. 21, a system is shown wherein the fiber bundle and proximal and distal optics both rotate independently of one another. Only a portion of the housing 102 is shown. The multifiber 20 is rotatably secured to a pulley 140 which is driven by a motor 142. The fiber 20 is rotated at 30 rps within a sleeve 144, again bearings, retaining collars and the like not shown. The inner sleeve is received within an outer sleeve 146. The outer sleeve 146 is fixed to the housing 102. The inner sleeve 144 has fixed at its distal end 148, a Selfoc lens 158, at about the same diameter as the bundle and with a field angle of 60° inclusive, to which is secured a holographic grating 160 which throws first order green light at an angle of 30°. A pulley 164 rotates the inner sleeve 144 at 15 rps. The pulley 164 is driven by a motor 166. A third pulley 170 is secured to a Selfoc lens 172, with a diameter twice that of the distal Selfoc lens, for rotation therewith at a speed of 15 rps. Secured to the lens 172 is a grating with first order green at 15°. These components are mounted within the housing for rotation. The pulley 170 is driven by the motor 176. The third pulley drives the proximal optics in synchronism with the distal optics. The third pulley results from the awkwardness of mechanically attaching 142 to the proximal optics.

The foregoing description has been limited to a specific embodiment of the invention. It will be apparent, however, that variations and modifications can be made to the invention, with the attainment of some or all of the advantages of the invention. Therefore, it is the object of the appended claims to cover all such variations and modifications as come within the true spirit and scope of the invention.

Having described my invention, what I now claim is:

1. A fiberoptic endoscope scanning system which comprises:
   at least one multifiber for transmitting light form an object within a field o view from the distal end to the proximal end;
   distal optics to form an image of the object on the distal end of the multifiber;

means to effect a first scanning mode of said multifiber to sweep out sequentially a continuous region of the object;

means to effect simultaneously a second distinct scanning mode to sweep out a region of the object;

wherein the first scanning mode is rotatable about the longitudinal axis of the multifiber and the second scanning mode is a chromatic scan; and optics at the proximal end for displaying the image substantially free of noise.

2. The system of claim 1 wherein the chromatic scan is non-rotatable.

3. The system of claim 1 wherein the chromatic scan is rotatable.

4. The system of claim 3 which comprises:

means to effect the first and second scans at the same angular velocity.

5. The system of claim 1 wherein the means to effect the chromatic scan comprises a prism.

6. The system of claim 1 wherein the means to effect the chromatic scan comprises a grating.

7. The system of claim 1 wherein the means to effect the chromatic scan comprises a grating in combination with a prism.

8. The system of claim 1 wherein the means to effect the chromatic scan includes means to tip the field of view.

9. The system of claim 1 wherein the means to effect the chromatic scan includes means to disperse the principle ray.

10. The system of claim 1 which includes:

means to mask at least a portion of the multifiber along its Y axis.

11. The system of claim 1 which comprises:

means for sequentially displaying the light received at the proximal end so that the region of the image scanned at the distal end is reconstructed at the proximal end.

12. The system of claim 1 which comprises:

means for effecting the scans at the proximal end in synchronism with the scans at the distal end and in a substantially identical pattern.

13. The system of claim 1 which includes proximal optics which are conjugate to the distal optics.

14. The system of claim 1 wherein the multifiber carries the light to illuminate the object whose image is formed in the image plane.

15. The system of claim 1 wherein the multifiber comprises a plurality of adjacent cores having different indices of refraction.

16. A method of scanning an object with a fiberoptic scanning system which includes:

transmitting light from an object within a field of view from the distal end of a multifiber to the proximal end;

forming an image of the object on the distal end of the multifiber;

scanning the object to sweep out sequentially a continuous region of the image in a first scanning mode; scanning simultaneously in a second distinct scanning mode to sweep out the region of the object;

rotating the multifiber about its longitudinal axis in the first scanning mode and scanning in the second mode about a second axis displaced from the first axis; and displaying the image at the proximal end substantially free of noise.

17. The method of claim 16 which includes: scanning chromatically in the second mode.

18. The method of claim 17 wherein the chromatic scan is rotatable.

19. The method of claim 18 which includes:

scanning in the first and second modes at the same angular velocity.

20. The method of claim 16 which includes: scanning chromatically to tip the field of view.

21. The method of claim 16 which includes: dispersing the principle ray.

22. The method of claim 16 which includes:

displaying the light received at the proximal end so that the region of the image scanned at the distal end is reconstructed at the proximal end.

23. A fiberoptic endoscope scanning system which comprises:

at least one multifiber for transmitting light from an object within a field of view from the distal end to the proximal end;

distal optics to from an image of the object on the distal end of the multifiber;

means to effect a first scanning mode o said multifiber to sweep out sequentially a continuous region of the object;

means to effect simultaneously a second distinct scanning mode to sweep out a region of the object;

wherein the first scanning mode is rotatable about a first axis and the second scanning mode is rotatable about a second axis displaced from the first axis; and optics at the proximal end for displaying the image substantially free of noise.

* * * * *